United States Patent [19]
Benedetti

[11] Patent Number: 6,155,443
[45] Date of Patent: *Dec. 5, 2000

[54] CONTAINER WITH CONTROLLED OPENING MECHANISM

[75] Inventor: Giovanni Benedetti, Ayrshire, United Kingdom

[73] Assignee: Wallace Cameron & Co. Ltd., Glasgow, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/080,882

[22] Filed: May 18, 1998

[51] Int. Cl.[7] .................................................. B65D 43/00
[52] U.S. Cl. ......................... 220/4.22; 220/829; 220/830
[58] Field of Search ................................ 220/4.22, 4.02, 220/810, 829, 830, 831

[56] References Cited

U.S. PATENT DOCUMENTS

| | | | |
|---|---|---|---|
| D. 359,863 | 7/1995 | Marlor | D6/451 |
| 2,208,158 | 7/1940 | Hiscock | 220/829 |
| 2,557,048 | 6/1951 | Haase | 220/830 |
| 4,114,236 | 9/1978 | Vandervort | 220/829 X |
| 4,381,063 | 4/1983 | Leong | 220/830 X |
| 4,470,220 | 9/1984 | Sudo | 49/379 |
| 4,822,965 | 4/1989 | Hyogo et al. | 220/830 X |
| 5,065,884 | 11/1991 | Naritomi et al. | 220/264 |

FOREIGN PATENT DOCUMENTS

| | | |
|---|---|---|
| 1 218 457 | 1/1971 | United Kingdom . |
| 1 299 680 | 12/1972 | United Kingdom . |
| 2059626 | 9/1996 | United Kingdom . |
| 2059627 | 9/1996 | United Kingdom . |
| 95/33392 | 12/1995 | WIPO . |

*Primary Examiner*—Steven Pollard
*Attorney, Agent, or Firm*—Ratner & Prestia

[57] ABSTRACT

A container for medical equipment, said container comprising a base and a lid pivotally connected together. A catch is provided on the lid and the base to hold them together according to a closed position. Upon release of the catch the lid is urged from a closed position to an opened position by at least one spring. Contacting surfaces providing predetermined frictional resistance are also provided onto the container to control the movement of the lid between the closed and the opened position.

6 Claims, 3 Drawing Sheets

CONTAINER WITH CONTROLLED OPENING MECHANISM

This invention relates to a container having a controlled opening mechanism, particularly a container holding medical equipment such as first aid materials.

Doors or lids which open automatically upon activation of a catch are already known and examples include the doors of car glove compartments, microwave oven doors, the doors to audio tape decks etc. Generally the continued opening of the door or lid is either assured by gravity or is aided by a biasing means, such as a spring. Where controlled opening is required (so that the door or lid opens at a slower rate than would otherwise occur) the decrease in the speed of opening is achieved by including a dampening unit in the opening mechanism. At present, the most widely available dampening unit is a sealed unit which comprises a fly wheel surrounded by a viscous material (eg grease or oil) and rotationally connected to a toothed cog which interacts with the opening mechanism of the door or lid in question. Thus, the opening door or lid is required to turn the fly wheel through the viscous material which thus provides a braking action.

Containers holding first aid equipment are of course also known, but the inclusion of an automatic controlled opening mechanism on such containers has not previously been perceived as desirable, and emphasis on mechanical simplicity has remained. We have found however inclusion that a controlled opening mechanism on first aid containers imparts a real benefit by simplifying the action needed to gain entry to the contents of the container and thus speeding access of the first aider to the required first aid equipment. Having the mechanism operating in a controlled fashion is desirable since this avoids the potential for accidents in a situation requiring a calm approach.

According to the present invention there is provided a container for medical equipment, the container having a means to open the container automatically and in a controlled manner.

More particularly the object of the invention is a container for medical equipment which comprises a base and a lid connected together by pivot means, whereby said lid and said base revolve about said pivot means between a closed position and an opened position. Catch means are provided on corresponding portions of said lid and said base, and cooperate together to hold the lid and the base in the closed position. The base and the lid are attached by biasing means whereby upon release of the catch means the lid is urged from the closed position towards the opened position by the biasing means. The container further comprises controlling means provided on the base and the lid to slow the revolving movement of the lid from the closed position to the opened position by frictional resistance.

According to a preferred embodiment, the frictional resistance is provided by contacting surfaces provided on the base and the lid and which are moved relative to each other as said lid is brought from the closed position to the opened position.

According to a further preferred embodiment, the pivot means comprises at least one shaft extending outwardly from the base and which passes through a corresponding aperture provided in the lid. A cap is attached at the extremity of the shaft which is sized and shaped sized and shaped with respect to said corresponding aperture so that the lid rotates between the closed position and the opened position. The controlling means comprises said cap and said aperture which are sized and shaped so that they contact each other and that their rotational movements with respect to each other provide a determined frictional resistance.

According to another preferred embodiment, the container further comprises a means to adjust the frictional resistance.

According to another preferred embodiment, the container further comprises a means to adjust the force provided by said biasing means.

According to another preferred embodiment, the container further comprises a means to slow the opening of the lid once a desired degree of opening has been achieved.

According to still another embodiment, the container further comprises stop means to limit the extent of opening of the lid.

More particularly, the container has a catch to retain the lid of the container in a closed position. When the catch is released the opening means is actuated. The container has a lid and a base which are pivotally joined together. The opening means comprises a biasing means and a controlled opening means. The biasing means is disposed between the lid and container to bias them apart, and thus to open the container when the catch is released. The catch can be attached to the base and can be biased against the lid, or vice versa.

The biasing means may comprise a spring such as a leaf spring or a torsion spring.

The controlled opening of the container is achieved by providing frictional resistance in the opening 1 mechanism, for example built into the pivot arrangement between the lid and container body. In one embodiment, the pivot arrangement may include two close fitting surfaces which move relative to each other as the lid of the container opens. Generally therefore a first surface will be part of (or connected to) the base and the second surface will be part of (or connected to) the lid of the container. Desirably the degree of closeness of the fit between the first and second surfaces may be adjustable, to increase or decrease the amount of frictional resistance provided thereby. In one embodiment the first surface is the inner surface of a circularly shaped collar and the second surface is the external surface of a tubular member which tapers slightly to one end. Thus, by varying the degree to which the tapering tubular member is inserted into the collar, the close fit of the two surfaces and the frictional resistance provided thereby alters accordingly.

Optionally, one of the surfaces is formed from acetyl and the other surface is formed from ABS; this combination of materials provides the required amount of frictional resistance to ensure the correct speed of opening of the container.

Optionally one of the two surfaces (for example the inner surface of the collar) may include a cam to further slow the speed of opening during the final stages.

Optionally one of the two surfaces may include a stop means to limit the full extent of the opening of the container lid.

The container may be wall-mounted and in this embodiment the controlled opening/biasing means combination is adjusted to take account of the effects of gravity on the opening lid. Alternatively, the container may be placed horizontally so that the lid needs to open upwards against the force of gravity. In this situation, the controlled opening/biasing means combination is selected to achieve the desired effect.

Optionally, the lid of the container may itself contain medical equipment (eg sticking plasters) and the controlled opening/biasing means combination is adjusted to take account of the additional weight which may be present in the container lid.

Optionally, the outer shape of the lid and base may be substantially as described in UK Registered Design Nos 2059626 or 2059627.

An embodiment of the invention will now be described by way of example, and with reference to the accompanying drawings, in which.

Figure 4A:
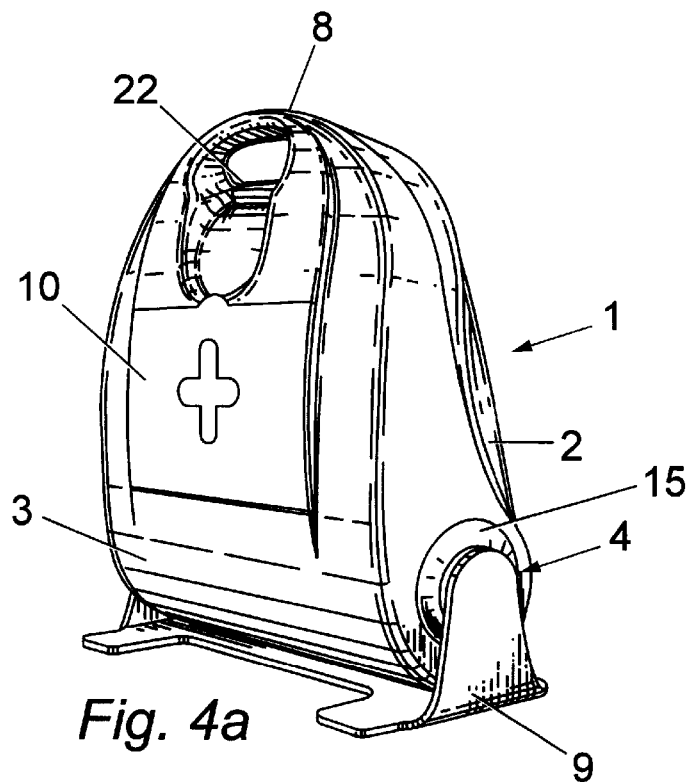
FIG. 4 shows (a) a perspective view (b) a side view and (c) a front view of the complete container.
Figure 4B:
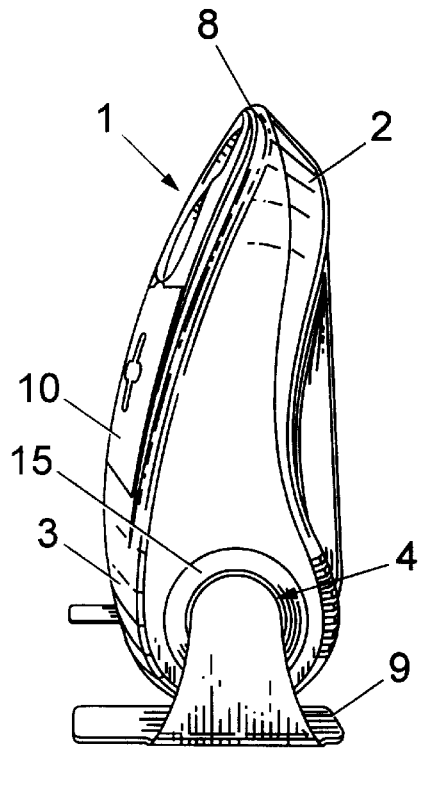
Figure 4C:
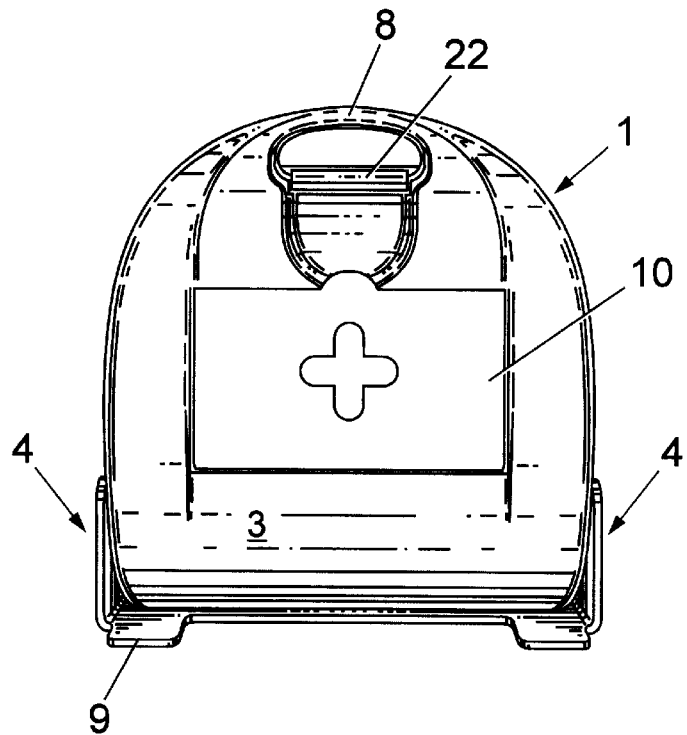

Referring now to FIGS. 4a to 4c, a container 1 has a base 2 and a lid 3. The base 2 and lid 3 are pivotally joined at a pivot point 4 such that the lid 3 can move pivotally to cover the base 2. The base 2 and lid 3 are locked together in a closed position by a catch 22 which can be of any known type, for example a clip or lock.

As is shown in FIGS. 4a to 4c, the lid 3 and base 2 each have a cut-away portion to provide a handle 8, and the lid 3 advantageously has a further cut-away portion for receiving a plaster box 10.

A stand bracket 9 is provided to mount the container 1 on a wall or to permit free standing on a horizontal surface. The stand/bracket may be removable.

Figure 1:
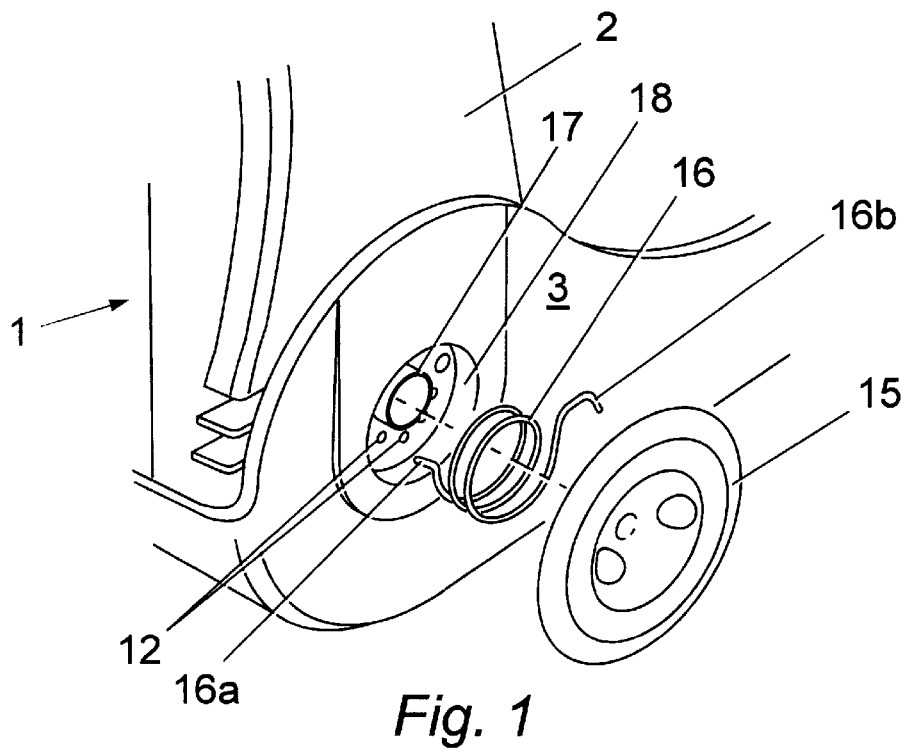
FIG. 1 is a partial perspective exploded view of the container, and showing the controlled opening mechanism.
Figure 2:
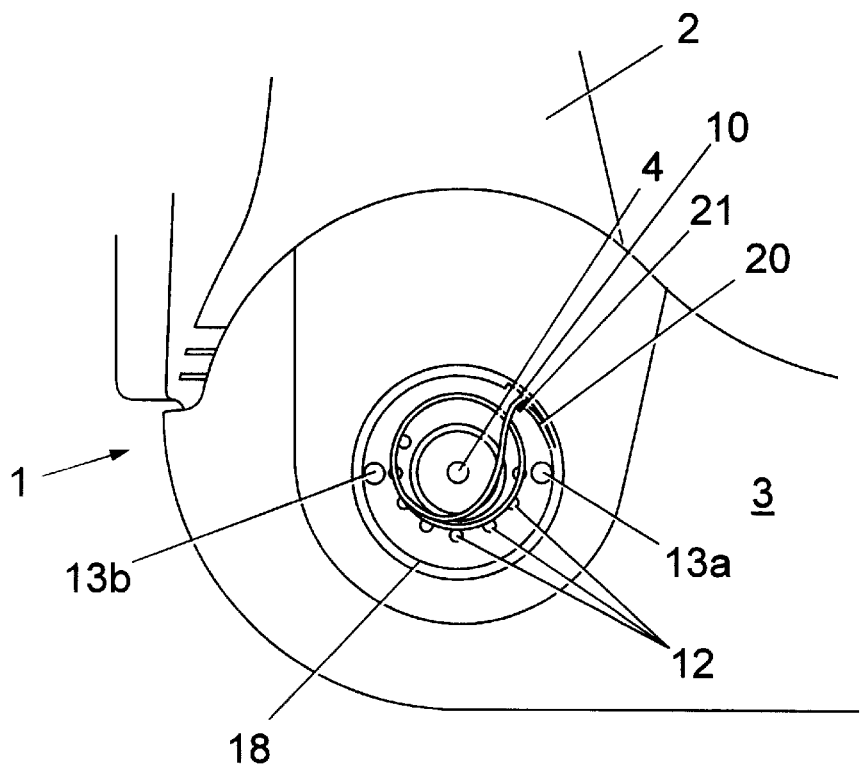
FIG. 2 is a side view of the controlled opening mechanism of the container, with the cap 15 removed.
Figure 3:
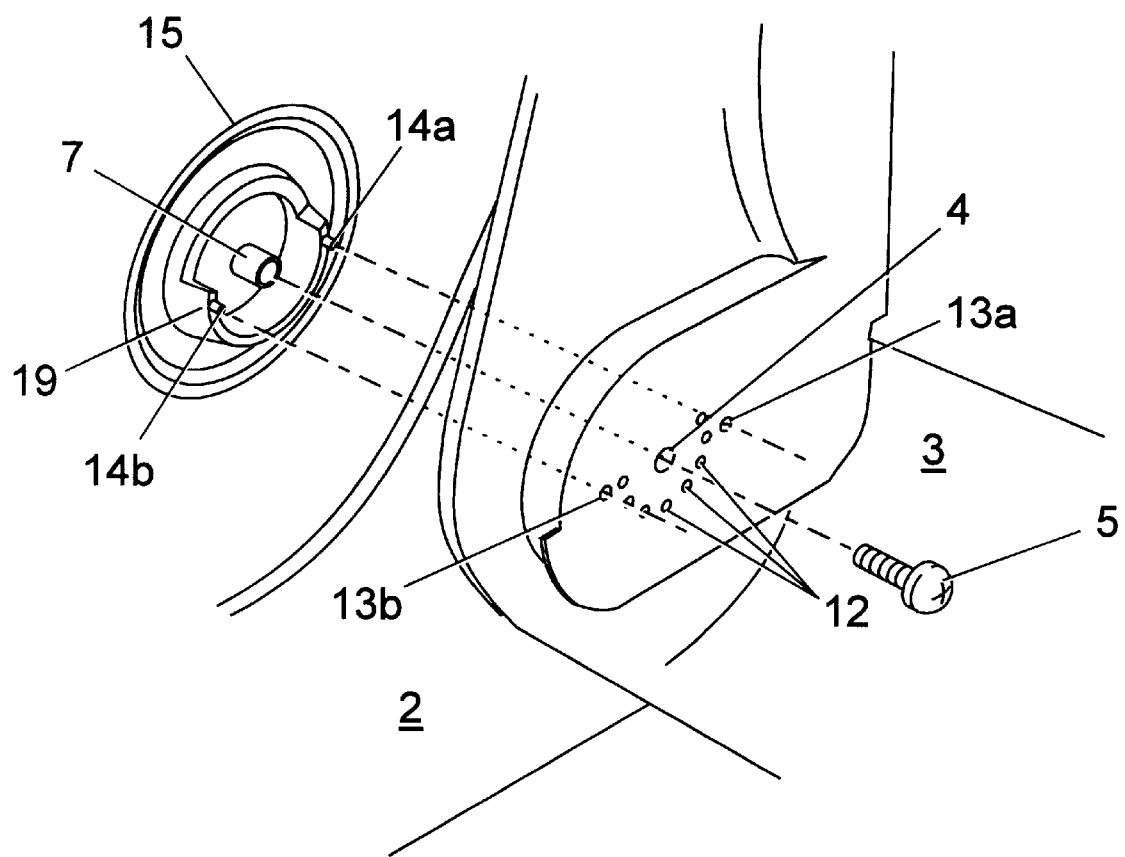
FIG. 3 show; the view from inside of the container, showing the position of cap 15.

With reference to FIGS. 1 to 3, the lid 3 is attached at each side of the base 2 by a couple of pivot means Each pivot means includes an inwardly-extending circular boss 18 on the lid 3 which fits within a corresponding circular housing (not shown) on the base 2. Within the housing the side wall of the base 2 has a series of holes 12 disposed at arcurate intervals, and a pair of diametrically-opposed apertures 13a, 13b. A central outwardly extending boss 17 is upstanding from the wall of the base 2, and a torsion spring 16 is disposed around the boss 17.

One end 16a of the spring locates within a selected one of the holes 12 (depending on the desired spring force) while the other end 16b is held in a slot 10 in the boss 18 on the lid 3.

A circular external cap 15 (see FIG. 3) has a pair of diametrically opposed pins 14a, 14b which fit within the apertures 13a, 13b and a screw 5 which extends through a central hole 4 in the side wall of the base 2 into a central boss 7 upstanding from an inner face of the cap 15, thereby to secure the pins 14a, 14b within the apertures 13a, 13b and prevent relative rotation of the cap 15 and the base 2 by rotation of the boss 24 within the housing (not shown) on the base 2.

The lid 3 is held closed on the base 2 by the catch 22, and when the catch 22 is released the torsion spring 16 provides enough force to urge the lid 3 from its closed position to its (open position by rotation relative to the cap 15 and base 2.

Controlling means, to speed up or slow the pivoting movement of the lid 3 with respect to the base 2 includes the inner face of the circular boss 18. As can be seen in FIG. 3, the inner face of the boss 18 forms a close fit with the outer face of a corresponding, very slightly tapering, arc-shaped collar 19 on the cap 15. The collar 19 tapers inwardly slightly away from cap 15 such that the depth of the positioning of the cap 15 in the boss aperture 18 (adjusted by tightening the screw 5) determines the closeness of the fit between the faces 18 and. 19 and thus the degree of frictional resistance between the cap 15 (and thus the base 2) and the lid 3 of the container 1.

The boss 18 includes a cam 20 which extends into the boss 18 and increases the degree of frictional resistance experienced by the lid 3 once a particular degree of opening has been achieved. Thus, where the lid 3 is urged open by the combined effects of gravity and the torsion spring 16, the cam 20 ensures that, rather than the lid 3 accelerating as it continues to open, a controlled manner of opening is maintained. As the co-operating surfaces of the boss 18 and the collar 19 rotate relative to each other, once a predetermined degree of rotation (and thus opening) has been achieved, the collar 19 engages with the cam 20 and the frictional resistance between the surfaces 18, 19 increases. Further rotation brings an end face of the arc-shaped collar 19 into contact with stop means, in the form of a small protuberance 21 which prevents further relative movement and limits the extent of opening of the lid 3.

A corresponding arrangement appears on the alternative side of the container.

In an alternative embodiment a leaf spring may replace the torsion spring. The leaf spring may have a bend of around 100°. The first end of the spring may be located in a slot on the interior of the base 2 so that the base. The other end of the spring may abut the inner edge of the lid 3 and can slide against it along a path defined on the lid. Optionally, the lid can be moulded to incorporate the path. The path can be greased to facilitate sliding of the spring end against the lid interior.

The leaf spring can be retained on the lid and can slide against the base, or alternatively, the spring can be located on another part of the apparatus, such as the cap 15, and can slide against the base or the lid.

Modifications and improvements can be incorporated without departing from the scope of the invention. For example, pens and accident report books/first aid advice can also be stored on the container.

I claim:

1. A container for medical equipment, said container comprising:

a base and a lid connected together by pivot means, whereby said lid and said base revolve about said pivot means between a closed position and an opened position;

catch means provided on corresponding portions of said lid and said base, said catch means cooperating together to hold the lid and the base in the closed position;

biasing means attached to said base and said lid whereby upon release of the catch means the lid is urged from the closed position towards the opened position by said biasing means;

controlling means provided on the base and the lid to slow the revolving movement of said lid from the closed position to the opened position by frictional resistance, the frictional resistance provided by contacting surfaces provided on the base and the lid and which are moved relative to each other as said lid is brought from the closed position to the opened position; and the pivot means comprises at least one shaft extending outwardly from the base and which passes through a corresponding aperture provided in said lid, and wherein a cap is attached at the extremity of the shaft, said cap being sized and shaped with respect to said corresponding aperture so that the lid rotates between the closed position and the opened position; and wherein said controlling means comprises said cap and said aperture which are sized and shaped so that they contact each other and that their rotational movements with respect to each other provided a determined frictional resistance.

2. A container as claimed in claim 1, wherein means to adjust the frictional resistance is provided.

3. A container as claimed in claim 1, wherein said biasing means is a torsion spring.

4. A container as claimed in claim 1, wherein means to adjust the force provided by said biasing means is provided.

5. A container as claimed in claim 1, wherein means to slow the opening of the lid once a desired degree of opening has been achieved is provided.

6. A container as claimed in claim 1, wherein stop means to limit the extent of opening of the lid is provided.

* * * * *